(12) United States Patent
Bosma et al.

(10) Patent No.: US 6,443,972 B1
(45) Date of Patent: Sep. 3, 2002

(54) VASCULAR FILTER

(75) Inventors: Gjalt Bosma, Opeinde; Hendrik G. Breedveld, Groningen, both of (NL); Thomas W. Duerig, Fremont, CA (US)

(73) Assignee: Cordis Europa N.V. (NL)

( * ) Notice: Subject to any disclaimer, the term of this patent is extended or adjusted under 35 U.S.C. 154(b) by 0 days.

(21) Appl. No.: 09/530,535

(22) PCT Filed: Nov. 13, 1998

(86) PCT No.: PCT/US98/24305

§ 371 (c)(1),
(2), (4) Date: Jul. 10, 2000

(87) PCT Pub. No.: WO99/25252

PCT Pub. Date: May 27, 1999

(30) Foreign Application Priority Data

Nov. 19, 1997 (NL) .................................... 1007584

(51) Int. Cl.⁷ ............................................ A61M 29/00
(52) U.S. Cl. ...................................................... 606/200
(58) Field of Search ................................ 606/200, 110, 606/113, 127, 114; 623/1; 604/96, 104

(56) References Cited

U.S. PATENT DOCUMENTS

| 4,425,908 | A | 1/1984 | Simon |
| 4,494,531 | A | 1/1985 | Gianturco |
| 4,662,885 | A | 5/1987 | DiPisa, Jr. et al. |
| 4,793,348 | A | 12/1988 | Palmaz |
| 4,832,055 | A | 5/1989 | Palestrant |
| 4,873,978 | A | 10/1989 | Ginsburg |
| 4,943,297 | A | 7/1990 | Saveliev et al. |
| 4,957,501 | A | 9/1990 | Lahille et al. |
| 4,969,891 | A | 11/1990 | Gewertz |
| 4,990,156 | A | 2/1991 | Lefebvre |
| 5,108,418 | A | 4/1992 | Lefebvre |
| 5,133,733 | A | 7/1992 | Rasmussen et al. |
| 5,147,379 | A | 9/1992 | Sabbaghian et al. |
| 5,234,458 | A | 8/1993 | Metais |
| 5,242,462 | A | 9/1993 | El-Nounou et al. |
| 5,300,086 | A | 4/1994 | Gory et al. |
| 5,329,942 | A | 7/1994 | Gunther et al. |
| 5,350,398 | A | 9/1994 | Pavcnik et al. |
| 5,370,657 | A | 12/1994 | Irie |
| 5,397,310 | A | 3/1995 | Chu et al. |
| 5,413,586 | A | 5/1995 | Dible et al. |
| 5,415,630 | A | 5/1995 | Gory et al. |
| 5,531,788 | A | 7/1996 | Dibie et al. |
| 5,601,595 | A | 2/1997 | Smith |
| 5,626,605 | A | 5/1997 | Irie et al. |
| 5,634,942 | A | 6/1997 | Chevillon et al. |
| 5,669,933 | A | 9/1997 | Simon et al. |
| 5,683,411 | A | 11/1997 | Kavteladze et al. |
| 5,695,518 | A | 12/1997 | Laerum |
| 5,709,704 | A | 1/1998 | Nott et al. |

(List continued on next page.)

FOREIGN PATENT DOCUMENTS

| DE | 40 30 998 A1 | 4/1991 | |
| DE | 195 09 464 C1 | 6/1996 | |
| EP | 0 462 008 A1 | 12/1991 | |
| EP | 0 815 803 A1 | 1/1998 | |
| FR | 2 606 642 A! | 6/1988 | |
| FR | 2 718 950 A1 | 10/1995 | |
| WO | 95/09567 | 4/1995 | |
| WO | 96/17634 | 6/1996 | |
| WO | 98/02112 | 1/1998 | |
| WO | WO 00/67669 | * 11/2000 | ............. A61F/2/01 |

Primary Examiner—Michael J. Milano
Assistant Examiner—Vy Q. Buf

(57) ABSTRACT

The present invention relates to a vascular filter (1) which can beplaced in a blood vessel, and which comprises at least one passage with a circumference suitable for the purpose of intercepting thrombus, wherein the filter (1) comprises a longitudinal body member (6) with, in a position of use, a circumference corresponding to the internal diameter of the blood vessel transverse to the longitudinal direction thereof. The invention also relates to a method for manufacturing vascular filter (1).

5 Claims, 7 Drawing Sheets

U.S. PATENT DOCUMENTS

| | | |
|---|---|---|
| 5,720,764 A | 2/1998 | Naderlinger |
| 5,746,767 A | 5/1998 | Smith |
| 5,800,457 A | 9/1998 | Gelbfish |
| 5,836,969 A | 11/1998 | Kim et al. |
| 5,853,420 A | 12/1998 | Chevillon et al. |
| 6,077,274 A * | 6/2000 | Ouchi et al. ................. 606/113 |
| 6,245,012 B1 * | 6/2001 | Kleishinski ................. 606/200 |
| 6,277,139 B1 * | 8/2001 | Levinson et al. ............ 606/200 |

* cited by examiner

VASCULAR FILTER

BACKGROUND AND SUMMARY OF THE INVENTION

1. Technical Background

This application is a National Phase filing under 35 U.S.C. 371 of International Application No. PCT/US98/24305, filed Nov. 13, 1998, based upon Netherlands Application No. 1007584 filed Nov. 19, 1997.

The present invention relates to a vascular filter which can be temporarily placed inside a blood vessel for the purpose of intercepting thrombus.

2. Discussion

Some basic types of vascular filters are generally known, wherein a single filter element or member extends substantially transverse to the direction of flow inside the blood vessel, and is wedged against the blood vessel wall due to the fact that it has a dimension slightly larger than the inside diameter of the blood vessel. Vascular filters may often be used in the vena cava, and may be described in such event as a "vena cava filter."

Known vascular filters may have some disadvantages, some of which may relate to their reliability. As such, known vascular filters may consist of a network of interconnected ribs, which extend substantially in a radial direction in relation to the blood vessel. Unfortunately, the entire filter may shift position if one of the ribs breaks. In addition, the free ends of the ribs, which are positioned under a certain pressure against the internal wall of the blood vessel, may cause trauma to the vessel wall, or may become embedded in it which may involve risk for the patient.

Another disadvantage of known vascular filters may be a possibility of shifting position in the blood flow inside the blood vessel, even when the filter maintains its proper shape, if a known vascular filter may have been incorrectly placed in a portion of the blood vessel which is too wide. In such an event, a vascular filter may not grab sufficient hold on the internal wall of the blood vessel.

Accordingly, an object of the present invention is to provide a vascular filter for delivery through a catheter in a compressed shape, where it tends to resiliently expand within the blood vessel. The vascular filter tends to trap thrombus or particles, and resist their movement further downstream. The filter includes, in a position of use, a circumference corresponding to the internal diameter of the blood vessel transverse to the longitudinal direction hereof.

With a vascular filter according to the present invention, the tubular section tends to wedge itself in place within the blood vessel, exerting pressure locally, along a large section of contact area, on the wall of the blood vessel. Accordingly, the filter tends to exert pressure on the internal wall of the blood vessel which could result in perforation of the blood vessel, but tends to hold itself in place. The vascular filter will consequently tend not to shift position.

In addition, the vascular filter according to the present invention cannot rotate transversely or tilt over, which is another important advantage of the present invention. In a preferred embodiment, a vascular filter according to the present invention has preferably been formed out of one single piece, which provides advantages, including simplicity.

In another preferred embodiment, a vascular filter according to the present invention includes a first and second filter section, arranged on either side of a body member. The body member and the filter sections thus enclose a space. Due to the elongated shape of the vascular filter according to the present invention, and the arranging of the first and second section on either side of the body member, the present filter has an enhanced filtering effect. In other words, two opportunities have been created for intercepting thrombus moving inside the blood vessel. The position of the filter inside the vena cava or another the blood vessel is therefore not dependent on the route along which it has been introduced, as a result of which the physician concerned has more freedom when choosing a route for introducing the vascular filter.

Another embodiment of the vena cava filter according to the present invention incorporates the feature that, when seen in an axial direction, the passage has the shape of a regular polygon, and provides several smaller filtering "cells". The purpose of these filtering cells is to intercept thrombus moving inside the blood vessel.

The filter sections, as arranged according to an embodiment described above on either side of the tubular body section, are preferably identical in shape, thereby enhancing the simplicity of the vascular filter according to the present invention.

A vascular filter may have been made of a braiding of wire-like elements, or a single plate-like element having a series of cuts at places corresponding to the positions of passages, or a tubular element also having a series of cuts at places corresponding to the positions of passages. It is thus preferably possible to effect under the influence of heat at least deformation of the material and possibly expansion of the vascular filter, which may be made in one of three ways mentioned, to obtain the ultimate shape and in particular the circumference hereof. Possible junctions are preferably effected by melting or welding free ends together, or by employing such a cutting pattern that the basic shape of the vascular filter according to the present invention is obtained. In addition, an advantage of the filter made of a tubular body is that it can be reduced to the dimensions of the tubular body, which dimensions may be very small, so that also the dimensions of the catheter required to introduce the filter may be very small.

It should be noted that the present invention also relates to methods for manufacturing vascular filters as described herein.

These and various other objects, advantages and features of the invention will become apparent from the following description and claims, when considered in conjunction with the appended drawings.

The invention will be explained in greater detail below with reference to the attached drawings of a number of examples of embodiments hereof.

The following description of the preferred embodiments of the present invention is merely illustrative in nature, and as such it does not limit in any way the present invention, its application, or uses. Numerous modifications may be made by those skilled in the art without departing from the true spirit and scope of the invention.

DETAILED DESCRIPTION OF THE PREFERRED EMBODIMENT

Figure 1:
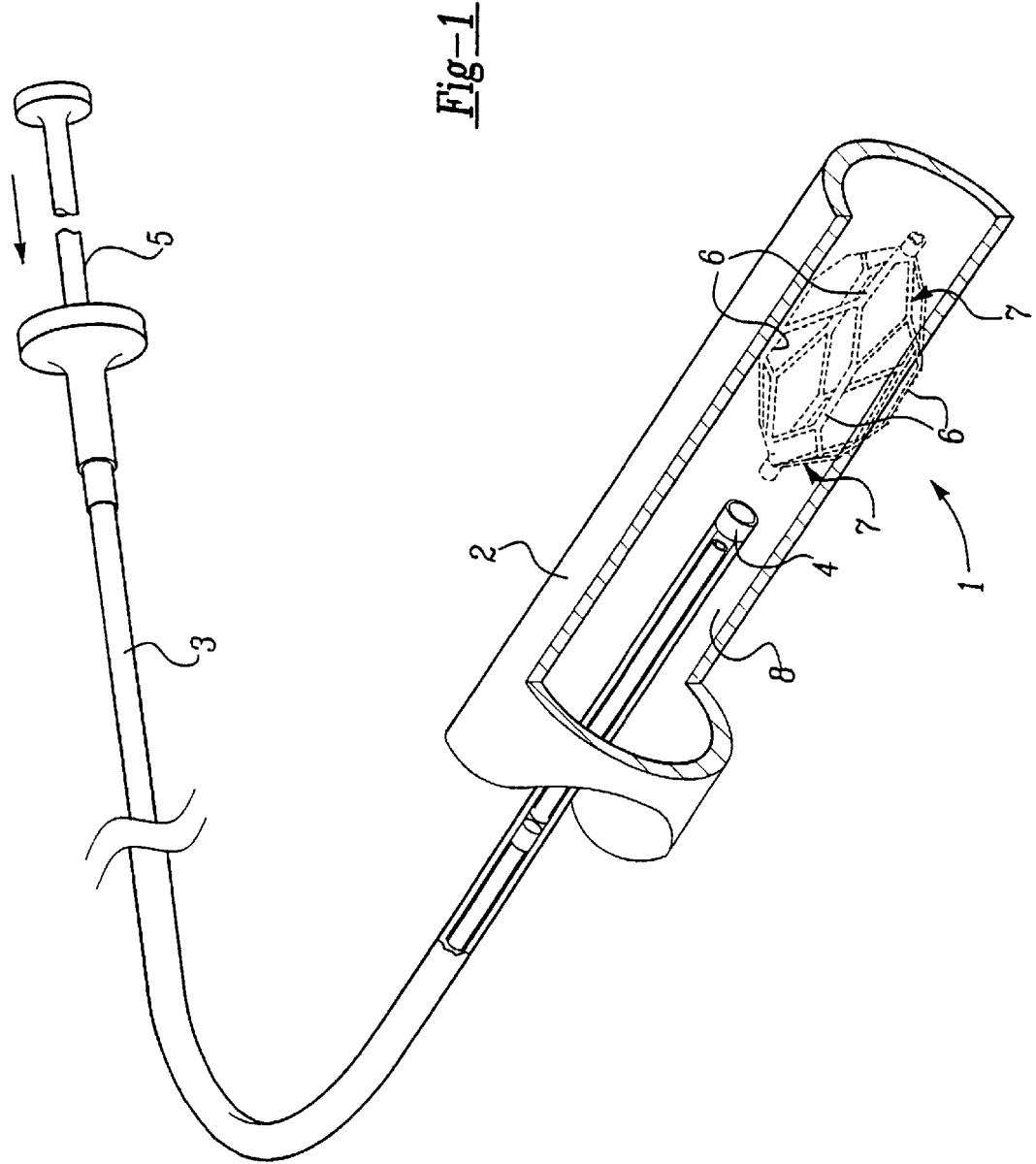
FIG. 1 shows a perspective view of a vascular filter in a position of use, and also illustrates schematically a manner in which the vascular filter may be placed inside a blood vessel.

In FIG. 1 a vascular filter 1 according to the present invention has been shown. In the situation illustrated here, the vena cava filter 1 has just been introduced into a blood vessel 2 by means of a catheter 3, which is substantially hollow and in which at least one vena cava filter has been arranged, in folded state, in the distal tip 4 hereof. By way of an alternative not illustrated here, it is also possible that the filter is pushed along the entire length of the catheter after the distal end hereof has been advanced to the required position. In this case the filter has preferably been packed in compressed state in transport packaging forming a covering. The vena cava filter is ejected by means of a-pushing wire 5 from the distal tip 4 of the catheter 3 and is introduced into the blood vessel where, due to the absence of the special limitation effective in the distal tip 4 of the catheter 3, the vena cava filter 1 will expand, under the influence of expansive forces inherent to the material of which the vena cava filter 1 has been made, into the shape illustrated here.

The vena cava filter illustrated here comprises a number of ribs 6 extending in an axial direction in relation to the blood vessel 2 and along the internal wall hereof. These ribs 6 form an elongated body member. On either side of the ribs 6, filters 7 have been arranged each forming a grid shape. Liquid inside the blood vessel can pass through in an unimpeded fashion, but thrombus are intercepted by one of the two filters 7.

A great advantage of this configuration is that it provides two chances at intercepting thrombus moving inside the blood vessel. In addition, due to the shape of the ribs 6, which extend along the internal wall of the blood vessel 2, it is ensured that there are no free ends of ribs which may damage the internal wall of the blood vessel 2 and possibly cause a trauma. The configuration of the vena cava filter according to the present invention illustrated is consequently designed so as to cause a minimum of damage to the blood vessel inside of which it is arranged. As the filters 7 have been arranged on either side of the ribs 6, a longitudinally symmetrical shape has been obtained. Accordingly, there is no difference as regards to whether the vena cava filter 1 is placed forward or backward inside the blood vessel 2. In other words, the proximal and distal ends of the filter are identical As has been illustrated here clearly, the grid shape of each of the filters 7 is such that each of the ribs 6 is connected to a number of the components of these filters 7. Furthermore, each of the ribs 6 is connected with both filters 7 on either side. Due to this configuration, even in the event that one of the ribs 6 or a component of one of the filters 7 may possibly break, the filter will tend not to shift position.

In addition, tipping over of both filters 7 has been avoided effectively due to the more or less tubular shape into which the ribs 6 have been arranged, so that positioning of the vena cava filter 1 inside the blood vessel 2 can take place with unprecedented stability and reliability.

In addition. the vena cava filter 1 has been made of a very resilient material, like nitinol, so that following deployment from the distal tip 4 of the catheter, it can expand and will be wedged against the internal wall 8 of the blood vessel 2.

Figure 2:
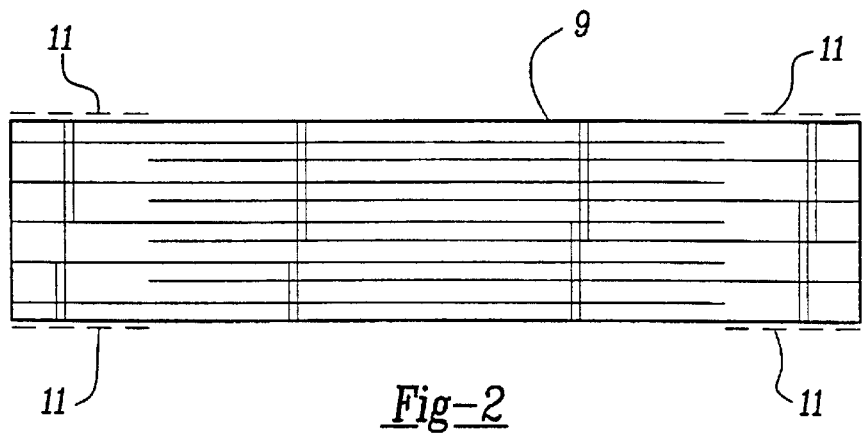
FIGS. 2 and 3 illustrate schematically preferable steps in the manufacturing of a second vascular filter according to the present invention.
Figure 3:
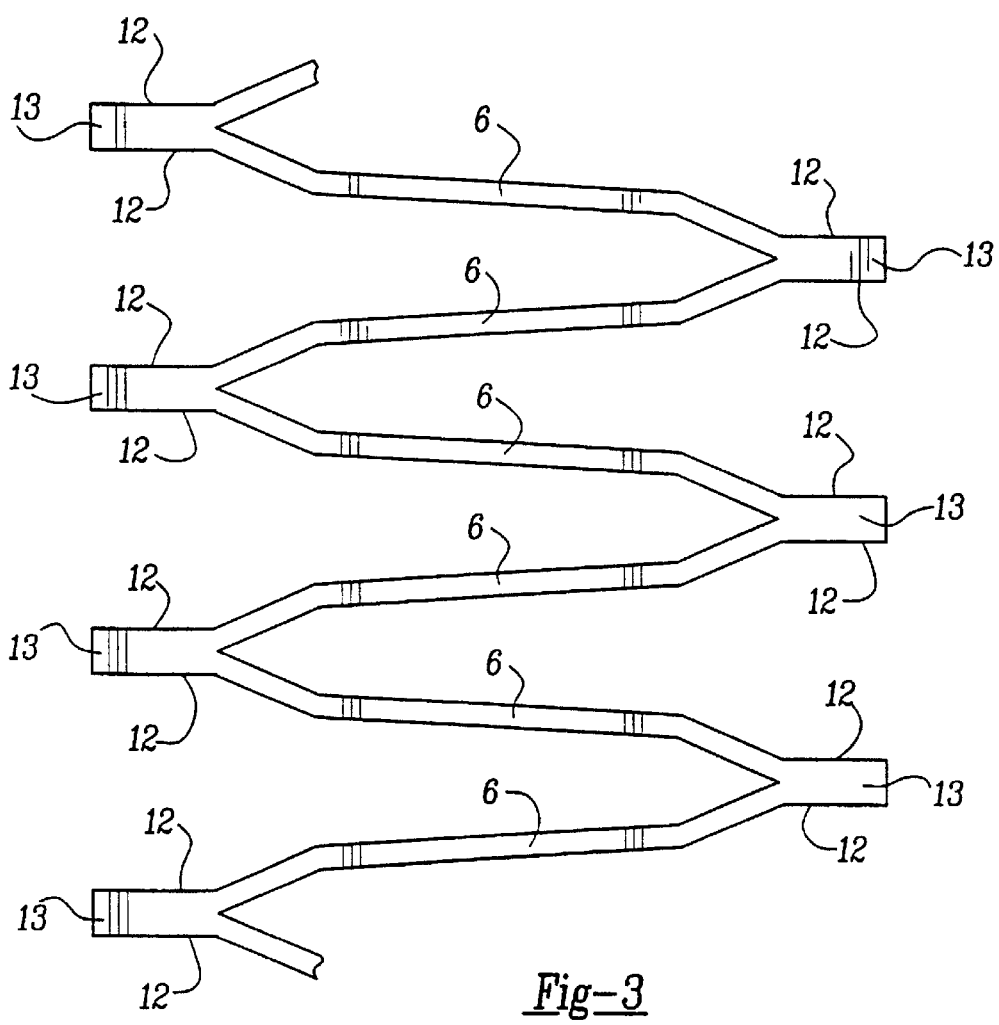

In FIG. 2, a plate 9 for a second embodiment of a vena cava filter according to the invention has been illustrated, which has been made of nitinol, and in which cuts 10 have been arranged. The cuts 10 extend alternately from one of the two sides of the plate 9 over a large section of the width of the plate 9, as has been illustrated in FIG. 2. When manufacturing a vena cava filter according to the present invention the plate 9 may be pulled apart under the influence of heat and in a deforming manner in such a way that a shape, of which a detail has been illustrated in FIG. 3, is obtained. Next this drawn out shape illustrated in FIG. 3 is arranged around a mold with a circular cross section, which mold has not been illustrated here, whereby both the welding strips 11 in FIG. 2 and the welding strips 12 at the ends 13, each of which has been connected to two ribs 6 as illustrated in FIG. 3, connect to one another respectively. To this end, the length of the mold (not illustrated here) is such that it corresponds to the length of the ribs 6 in FIG. 3 and the mould is consequently pill or cigar shaped allowing in particular the welding strips 12 to connect to one another. Next the welding strips 12 are connected to one another and the welding strips 11 are connected to one another by means of heat treatment in order to make these welding strips 11, 12 melt together respectively. Next, employing a method according to the present invention and whilst heating the configuration illustrated in FIG. 3 which is to be processed into a vena cava filter, of which the welding strips 11, 12 have been melted together respectively, the mould, not illustrated here and preferably made of a pliable material, is expanded in order to deform the material of which the vena cava filter is to be formed in this manner into a shape of which the central section, that is to say, the section corresponding to the ribs 6, has a larger diameter than the tips on either side, that is to say those sections corresponding to the ends 13.

After cooling, the vena cava filter thus formed retains the shape of the expanded (but not illustrated) mold and it will then be possible to fold the vena cava filter according to the present invention thus formed, in order to place it inside the distal tip of a catheter 3 for the purpose of introduction, as has been illustrated in FIG. 1.

Using nitinol ensures that the filter is very elastic, while it can be folded so as to occupy only a very limited space and expands independently to the diameter of the blood vessel after introducing it in the manner described above with reference to FIG. 1.

Using the mold ensures deformation of the basic shape of the material of which the vena cava filter is made, whereby elasticity of the vena cava filter thus formed manifests itself in relation to this new basic shape.

Figure 4:
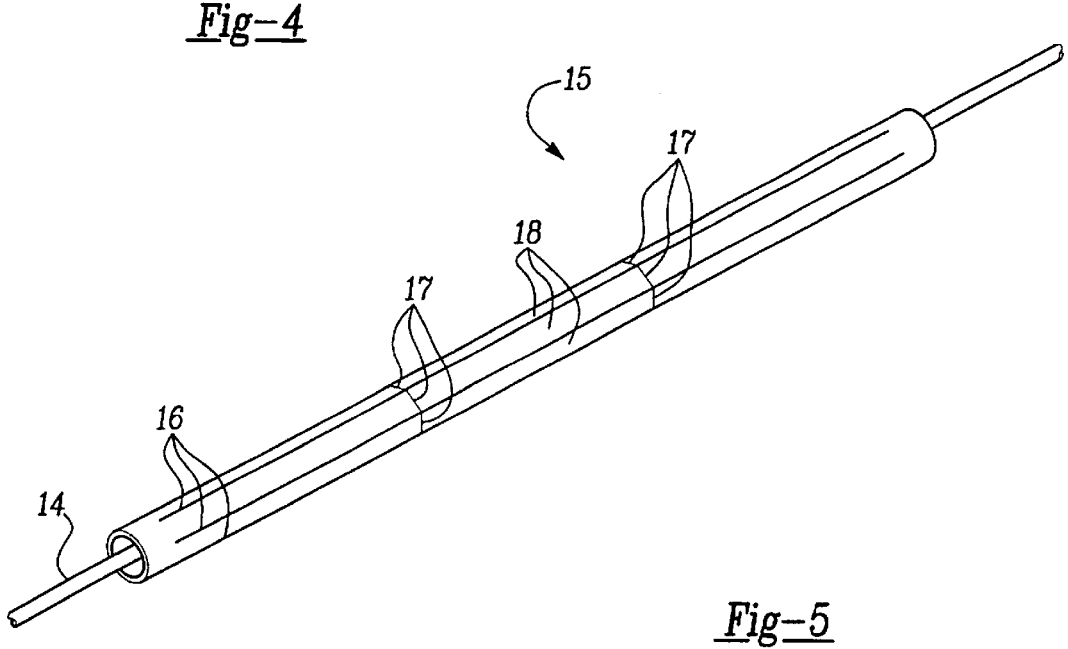
FIG. 4 shows a perspective view of a vascular filter according to the present invention, prior to being used.

In FIG. 4, a third embodiment of a vena cava 35 filter 15 has been illustrated in the state just prior to introduction into a blood vessel hereof. The vena cava filter 15 has been folded around a guidewire 14, whereby the vena cava filter 15 is freely movable along the guidewire 14. In FIG. 4, the catheter body itself has not been shown, but it is noted that the vena cava filter remains in the folded state illustrated here due to the space limiting effect exerted by the distal tip of this catheter body, inside of which the vena cava filter 15 is situated in its folded state.

Figure 5:
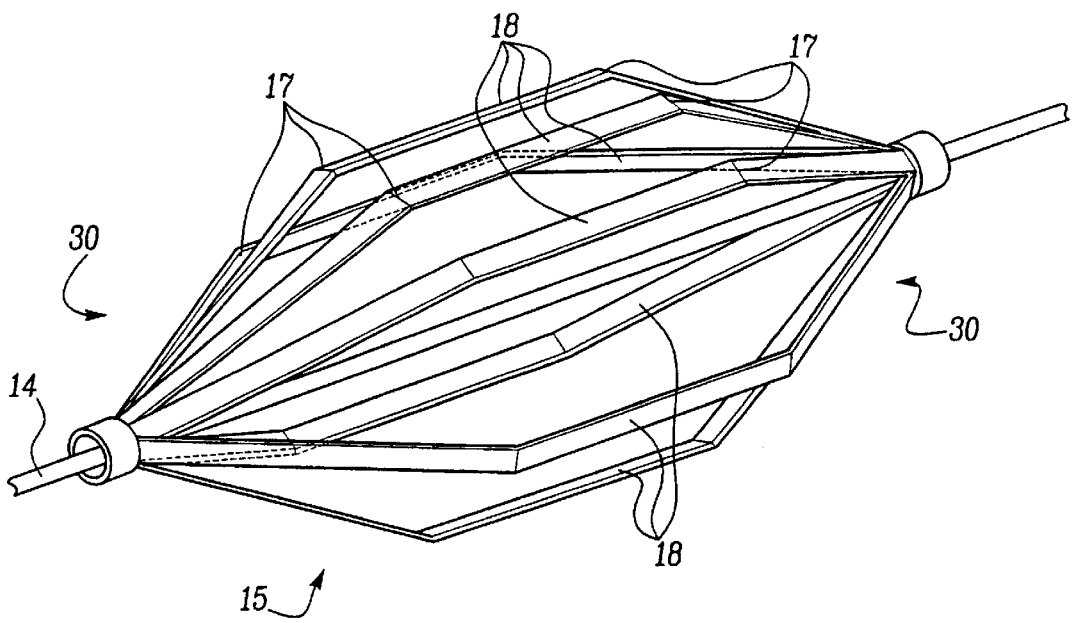
FIG. 5 shows a perspective view of a vascular filter illustrated in FIG. 4 when in use.

The vena cava filter 15 comprises cuts 16 extending in the longitudinal direction of the vena cava filter 15 between, but not as far as the ends of this vena cava filter. By means of the cuts, strips of material 18 have been defined, as illustrated in FIG. 5, which is an illustration of the vena cava filter 15 just following ejection from the catheter not illustrated here and its subsequent expansion. These strips 18 correspond to the ribs 6 as illustrated in the FIGS. 1 and 2, but comprise bending lines 17 which have been defined by the shape of the mold which has been used in the manufacturing process of the vena cava filter 15 illustrated here. The strips 18 consequently also form the filters 30 on either side of the filter 15. Those sections of the strips 18 forming the ribs extend in an axial direction and are connected on either side with a filter 30, which is formed between the bending lines 17 and the tips on either side of the vena cava filter 15.

Also in this case, possible breaking of a section of a strip 18 functioning as rib, or breaking of a section functioning as filter 7 cannot result in the vena cava filter shifting position which, in the state illustrated in FIG. 5, is still arranged over the guidewire 14, which is subsequently to be withdrawn after the correct positioning hereof. As long as the vena cava filter has been provided with more than two strips, the filter will tend not to shift position, due to the breaking of one of the strips; especially in the case of a uniform distribution in radial direction of the strips thus provided this is avoided in an effective manner.

The embodiment of the vena cava filter according to the present invention illustrated here also has the safety advantages of the tendency to prevent any free ends from occurring and damaging the internal wall of a blood vessel, and that these sections of the strips 18 extend as ribs along the internal wall of the blood vessel.

Figure 6:
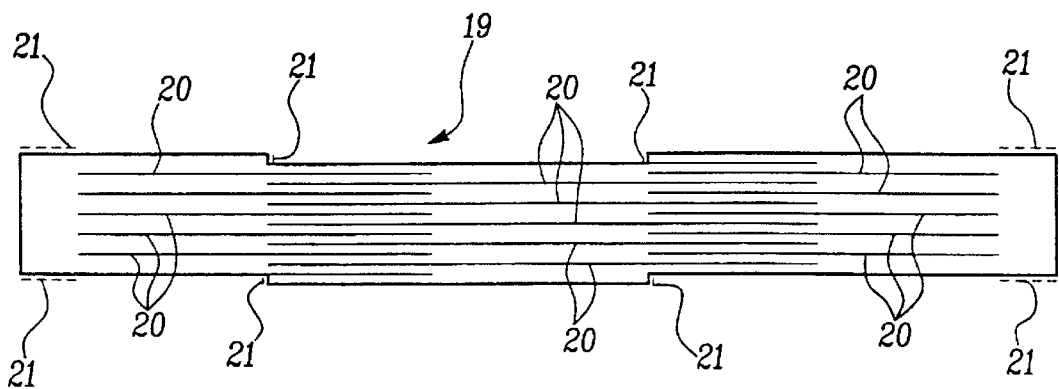
FIG. 6 shows a view of planar element for the manufacturing of a vascular filter according to the present invention.

In FIG. 6, a plate 19 for a fourth embodiment has been illustrated which shows an alternative in relation to the one which has been illustrated in FIG. 2. Also, this plate 19 includes cuts, although they are arranged in a different pattern to those in the plate illustrated in FIG. 2.

Figure 8:
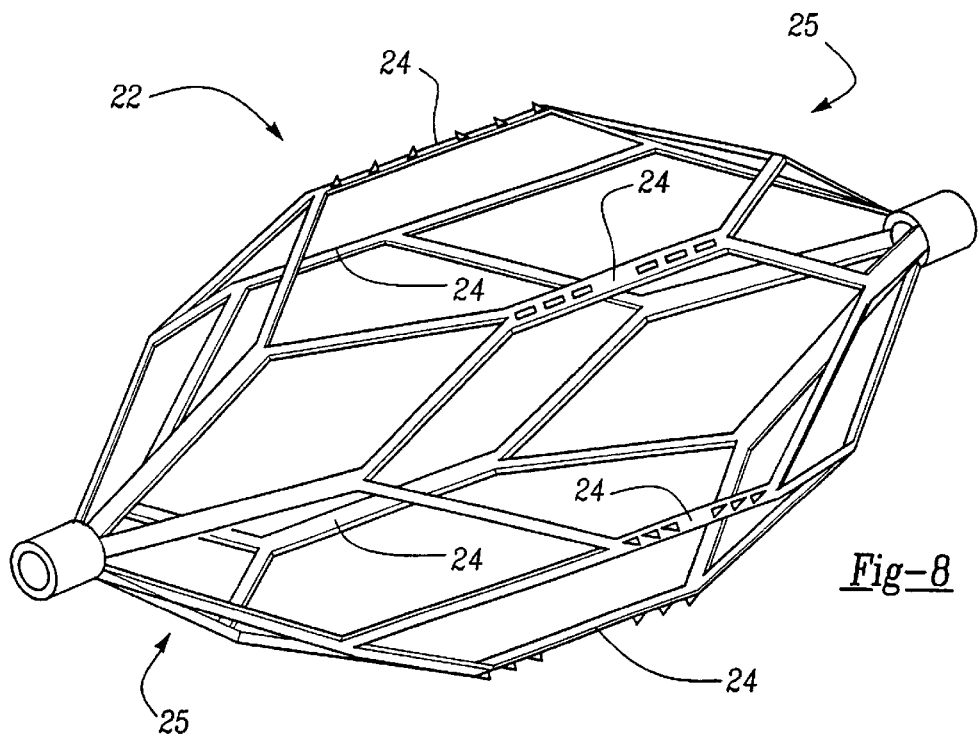

The plate 19 is arranged around an inflatable or expandable mold (not illustrated), the longitudinal direction of which corresponds to the transverse direction of the plate 19 illustrated in FIG. 6, and the cross-section of which is circular. The welding strips 21 are connected to one another for instance by means of melting them together. Accordingly, the vena cava filter 22 illustrated in FIG. 8 is obtained following expansion of the mold while heating the material of which the plate 19 has been made.

Figure 7:
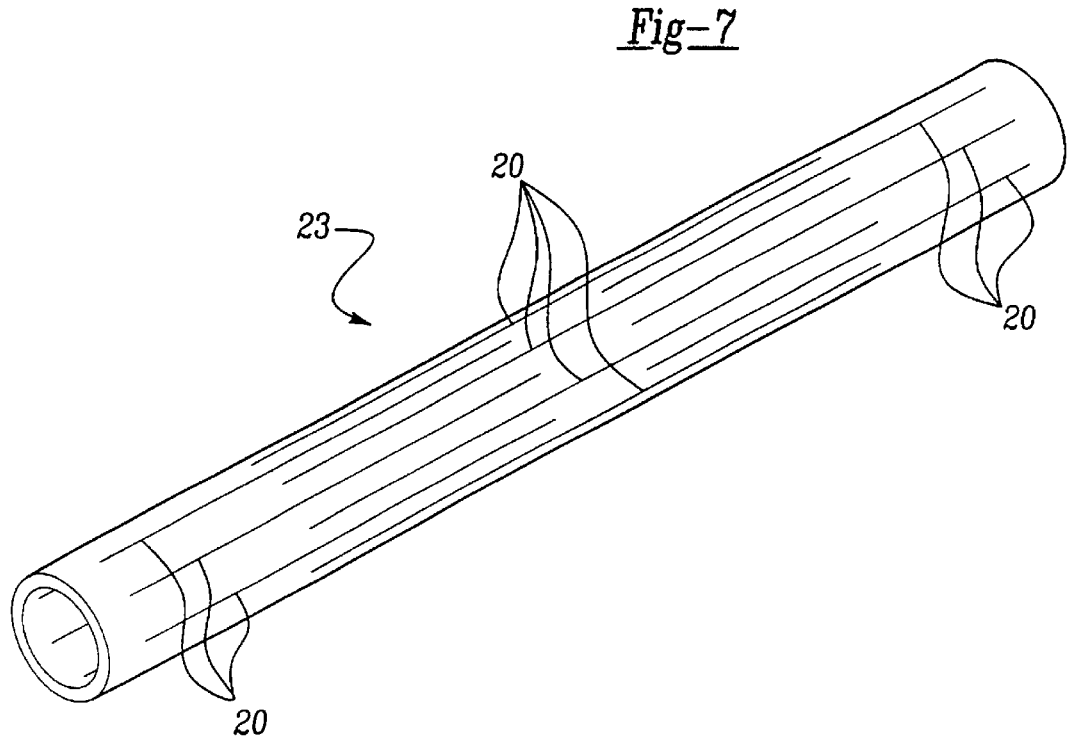
FIG. 7 shows an alternative embodiment for the production of the vascular filter of FIG. 6 out of a tubular shape according to the present invention and FIG. 8 shows a perspective view of the vascular filter of FIG. 6 according to the present invention.

After melting the welding strips 21 together, a tubular basic shape is obtained, which has been illustrated in FIG. 7 and is indicated with reference number 23. In addition, the basic shape 23 may also be obtained by arranging the pattern of cuts 20, as shown in the basic shape 23 in FIG. 7, in a tubular element which has been made of nitinol for instance. Thus the step of melting the welding strips 21 in FIG. 6 together is avoided, thus simplifying the procedure of manufacturing the vena cava filter according to the present invention considerably.

The vena cava filter ultimately formed, as illustrated in FIG. 8, once again comprises ribs 24, 35 just like the other embodiments of vena cava filters according the present invention illustrated in FIG. 1 and FIG. 5. Each of the ribs of the vena cava filter 22 in FIG. 8 is connected on either side with a number of components of filters 25. The filter thus displaying a grid shape with passages sufficiently large so as not to impede normal flow of liquid through the blood vessel, but small enough to intercept harmful blood clots or thrombus. In doing so, as has been described above, this filtering action occurs at two locations in the vena cava filter 22. In axial view, the passages in the network of the filters 25 display the shape of a diamond, parallelogram or polygon.

Figure 9A:
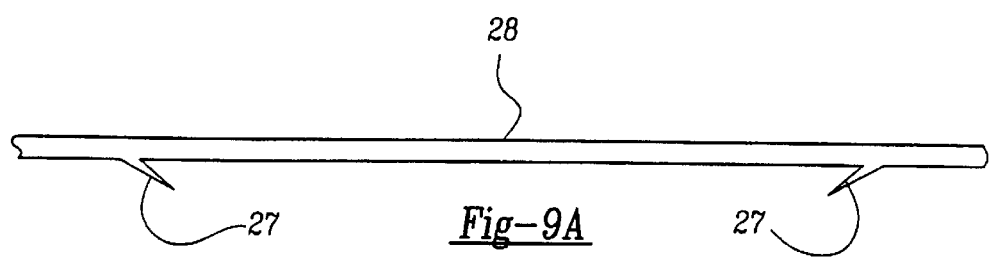
FIGS. 9A–9C are detailed views of portions of a vascular filter having hooks or friction members, according to the present invention.
Figure 9B:
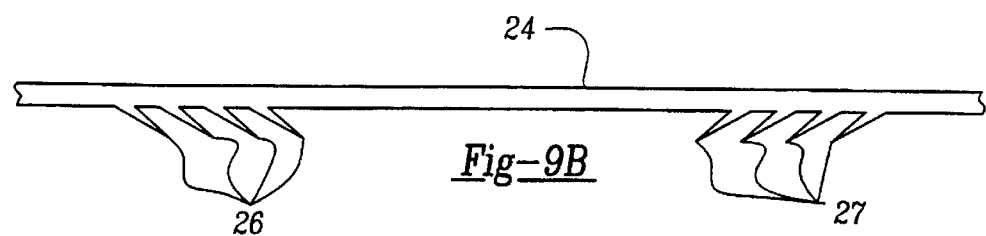
Figure 9C:
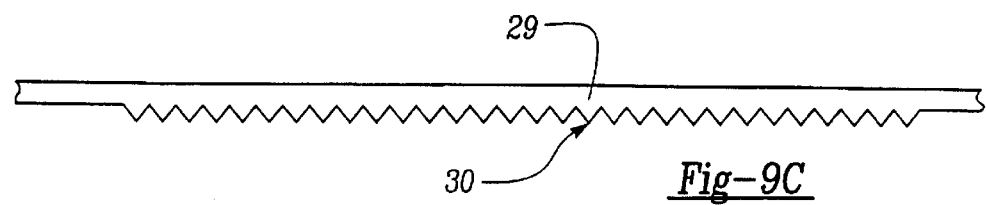

FIGS. 9A–9C illustrate further improvements to enhance the resistance of the vena cava filter against undesired displacement. In FIG. 9A for instance, a rib 28 of a vena cava filter according to the present invention has been illustrated, which has been provided with hooking elements 26 and 27 pointing in opposite directions. These hooking elements are sufficiently sized and small so that they ensure the proper grip on the internal wall of the blood vessel, but tend not to damage the latter.

Figure 10:
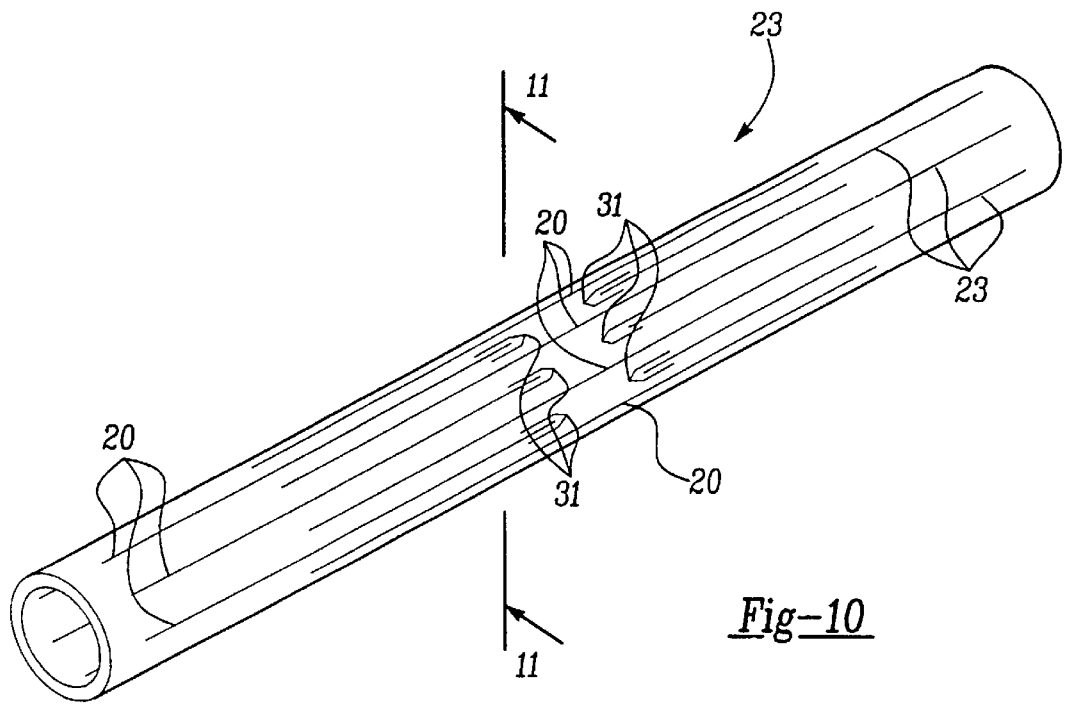
FIG. 10 shows a perspective view corresponding to another embodiment of the present invention.
Figure 11:
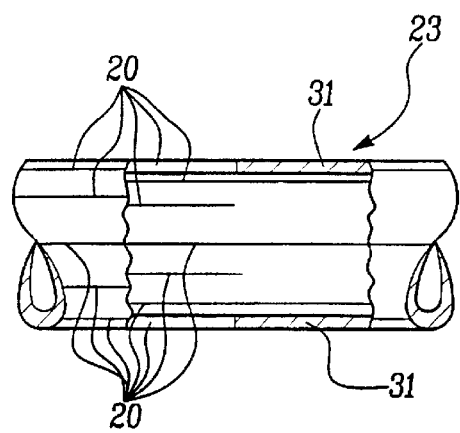
FIGS. 11 and 12A–B show cross-sectional views of the embodiment illustrated in FIG. 10.
Figure 12A:
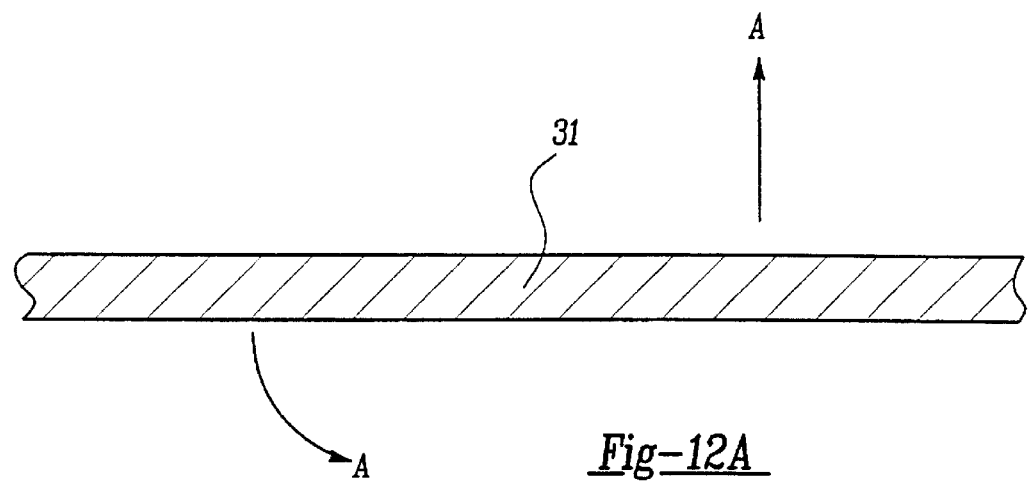
Figure 12B:
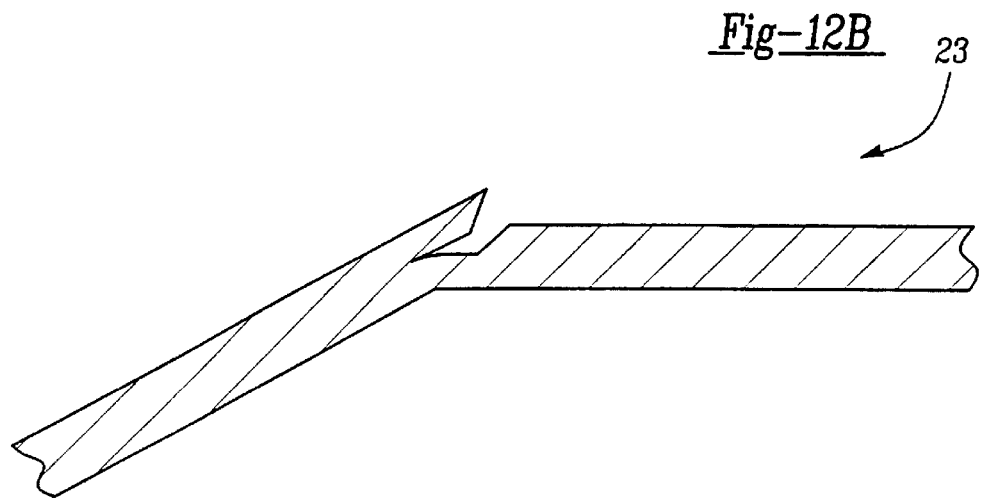

In particular, this embodiment can be manufactured advantageously by providing the tubular basic shape shown in FIG. 7 with additional notches, as illustrated in FIG. 10 and indicated with number 31. FIG. 11 shows a cross-sectional view along the line 11—11 in order to clarify the configuration of the notch 31. In FIG. 12 it has been illustrated that the notched sections of the tubular basic shape 23 bend outward during expansion hereof, to extend hooking elements similar to those indicated with number 27 in FIGS. 9A–C. FIG. 12A illustrates the situation prior to expansion, and FIG. 12B the situation immediately following expansion. In FIG. 12A, arrow A has been used to indicate the relative directions of sections of the basic shape 23 to the left and the right of the notch 31.

The notches 31 also provide attenuations in the material of which the basic shape 23 has been made, as a result of which bending is encouraged to occur at the sites of these attenuations.

In FIG. 9B, a rib 24 of the vena cava filter illustrated in FIG. 8 is shown. On each of the ribs 24, a number of hooking elements, pointing in opposite directions, have been arranged, which, for the sake of simplicity, have also been given the numbers 26 and 27, whereby a greater number of hooking elements may obviously increase the frictional resistance mentioned above.

In FIG. 9C yet another rib 29 is shown, which has been provided with a serrated profile 30, of which the teeth are not arranged in a preset direction but only extend outwards in relation to the vena cava filter, when in use, towards the internal wall of the blood vessel. Also, simple coarsening of the surface of the ribs concerned may suffice.

Each of the embodiments illustrated in the FIGS. 9A–9C aims at increasing the reliability of the anchoring of the filter, so that the vena cava filter according to the present invention will not shift position. Protrusions such as the projections 26 or 27 or the serrated profile 30 are pushed, due to the elasticity and the tendency of the vena cava filter to expand, into the internal wall of a blood vessel. Consequently, resistance against possible displacement under the influence of the flow of fluid or blood through the blood vessel is increased, and as a result the reliability is enhanced.

In the axial view, the filter sections on either side of the ribs of the vena cava filters according to the present invention described above display diamond or polygon shapes. It is also possible to suffice with vena cava filters of which the filter sections display in axial view a star shape (as illustrated in FIG. 5), or any other shape as long as they intercept blood clots or thrombus successfully. An advantage of this feature is that, after passing the first filter section and the tubular section or the elongated body member, a second chance at interception in the form of an additional filter section has been provided. Also, other shapes of the filter sections in axial view are possible, which shapes will occur to those skilled in the field after reading the present description. The shapes of the filter sections in axial view need not be symmetrical, and may have in principle any suitable appearance.

If it is desirable to be able to remove a vena cava filter introduced into a blood vessel at a later stage, a vena cava filter according to the present invention may be provided on one or both ends with a noose construction in order to extract the vena cava filter back into a catheter, by means of a hook member.

Furthermore, in connection with the method for manufacturing a vena cava filter according to the present invention, the step employing an expandable mold in order to effect the required shape of the vena cava filter has been described each time. It should be noted however, that it is also possible to use a mold which retains its shape, around which in advance sections, deformed under the influence of heat, have been arranged and if desired followed by a step including heating certain sections to such an extent that a vena cava filter, forming one single unit, is manufactured. In this respect one can think of using separate strips, which are arranged around a pill or cigar-shaped mold of the desired shape after heating the latter, in order to connect at least the tips to one another by melting them together. Furthermore, it is not necessary to deform sections of the vena cava filter in advance. Treatment, for instance heat treatment, only serves to fix the vena cava filter, and in particular sections hereof, in the new shape defined by the mold. This last alternative is particularly suitable for materials which are very elastic, like nitinol.

In addition to the nitinol mentioned so far, many other materials may also be used for manufacturing a vena cava filter according to the present invention. By way of alternative, various metals may for instance be used, in which case it is essential that the vena cava filter assumes the intended shape hereof after having been ejected from the catheter for the purpose of introduction hereof. The vena cava filter, during introduction, is of course kept in a folded state, by means of the catheter. To this end a configuration may be used decompressing the filter metal due to the elastic properties hereof.

Furthermore, retraction of a vena cava filter according to the present invention is mentioned above, which should not limit the scope of the claims attached. Vena cava filters according to the invention may for instance be anchored by means of a cord body, in which case this cord body is arranged at a site which can easily be reached from outside the body of a patient, so that removal can take place with a minimum of effort. As regards the subject of the invention it is therefore of no consequence whether the filter is placed permanently, in a removable manner, temporarily or otherwise.

What is claimed is:

1. A vascular filter, which can be placed inside a blood vessel and which comprises:

in a radially compressed state, a tubular metal cylinder having a first and second integral cylindrical end collar at a proximal and distal end of the vascular filter; a plurality of ribs arranged in a preselected pattern and extending between the first and second end collar in a direction parallel to a longitudinal axis of the vascular filter;

in radially expanded deployed state, the ribs tend to resiliently expand in radial directions, thereby causing the first and second end collars to move toward each other; each of the ribs tending to spread apart, such that the vascular filter defines a plurality of central parallel hexagon shapes arranged adjacently around a central circumference of the vascular filter, each of the ribs defining each hexagon shape extending in a plane parallel to the longitudinal axis of the vascular filter; the vascular filter further defining a first and second end filter portion connecting the central hexagons with the end collars, wherein the end filter portions each define a plurality of diamond shaped sections having four sides; each of the diamond shapes being formed by a first and second rib each forming a portion of a first and second of the central hexagon shapes, and by a first and second conical rib directly connecting an apex of the first and second of the central hexagon shapes with the end collars respectively; the conical ribs all extending along a first and second end cone;

whereby the first and second filter sections enhance the effectiveness of the vascular filter.

2. The vascular filter as claimed in claim 1, characterized in that the construction is such that it has been formed out of one single unitary metal element.

3. The vascular filter as claimed in claim 1, adapted for use in the vena cava.

4. The vascular filter as claimed in claim 1, characterized by anchors formed on at least one surface of the vascular filter directed outward in a radical direction.

5. A method for manufacturing a vascular filter comprising forming an cylindrical elongated body member out of one single element having a first and second unitary cylindrical end collar, and a plurality of structural ribs formed by a series of longitudinal cuts in the cylindrical body member with, in a position of use, a circumference corresponding to the internal diameter of the blood vessel and having a first and second conical end filter section for collecting and trapping thrombus.

* * * * *